United States Patent [19]

Schlosberg et al.

[11] Patent Number: 5,798,319
[45] Date of Patent: Aug. 25, 1998

[54] HIGH STABILITY AND LOW METALS ESTERS BASED ON 3,5,5-TRIMETHYL-1-HEXANOL

[75] Inventors: Richard Henry Schlosberg, Bridgewater, N.J.; David Wayne Turner; Martin Anthony Krevalis, both of Baton Rouge, La.; William Joseph Munley, Jr., Houston, Tex.; Haven Scott Aldrich, Annandale, N.J.

[73] Assignee: Exxon Chemical Patents Inc., Houston, Tex.

[21] Appl. No.: 586,117

[22] Filed: Jan. 16, 1996

[51] Int. Cl.$^6$ .................. C09K 7/00; C10M 105/32
[52] U.S. Cl. .................. 507/138; 507/139; 507/100; 507/116; 508/478; 508/482; 508/496; 508/498
[58] Field of Search .................. 507/138, 139, 507/100, 116; 508/482, 478, 480, 496, 498

[56] References Cited

U.S. PATENT DOCUMENTS

| Re. 28,805 | 5/1976 | Braid | 252/401 X |
|---|---|---|---|
| 2,517,351 | 8/1950 | Reid | 260/31.8 |
| 2,650,908 | 9/1953 | Beears | |
| 2,792,417 | 5/1957 | Dean | |
| 2,847,383 | 8/1958 | Airs et al. | 252/42.7 |
| 2,993,860 | 7/1961 | Critchely | 508/344 |
| 3,065,180 | 11/1962 | Pethrick et al. | 508/251 |
| 3,282,840 | 11/1966 | Foster et al. | 508/495 |
| 3,347,791 | 10/1967 | Thompson et al. | 508/203 |
| 4,851,144 | 7/1989 | McGraw et al. | 252/52 A |
| 5,185,092 | 2/1993 | Fukuda et al. | 252/56 S |
| 5,211,884 | 5/1993 | Bunemann et al. | 252/56 S |
| 5,397,488 | 3/1995 | Chen et al. | 252/56 S |
| 5,403,503 | 4/1995 | Seiki et al. | 252/52 A |
| 5,434,294 | 7/1995 | Pugach et al. | |

FOREIGN PATENT DOCUMENTS

| 0 376 997 | 1/1995 | European Pat. Off. | C07C 69/76 |
|---|---|---|---|
| 1093677 | 12/1967 | United Kingdom | |
| 2 216 541 | 10/1989 | United Kingdom | C09K 5/04 |

OTHER PUBLICATIONS

Database Crossfire—Beilstein Informationssyteme GmbH, BRN–3429005; XP002031015; see abstract & Ind. Eng. Chem, vol. 41, 1949, pp. 2860–2861, Bruner.

*Primary Examiner*—C. H. Kelly
*Attorney, Agent, or Firm*—John F. Hunt

[57] ABSTRACT

A lubricant which is prepared from at least one synthetic ester composition exhibiting thermal and oxidative stability which comprises the reaction product of 3,5,5-trimethyl-1-hexanol and an acid or anhydride; and a lubricant additive package; whereby the incorporation of an antioxidant in the lubricant additive package for the purpose of maintaining oxidative and thermal stability of the crankcase lubricating oil formulation to at least 20 minutes as measured by HPDSC at 220° C., 3.445 MPa air and 0.5 wt. % dioctyl diphenyl amine can be either reduced or eliminated. The synthetic ester composition preferably exhibits the following additional properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

44 Claims, No Drawings

HIGH STABILITY AND LOW METALS ESTERS BASED ON 3,5,5-TRIMETHYL-1-HEXANOL

The present invention generally relates to a high stability ester base stock (e.g., phthalates, adipates, trimellitates, isophthalates, terephthalates, acetates, propionates, carbonates, sebacates, complex alcohol esters, complex acid esters, oxo acid esters and linear acid esters) for use in passenger car motor oils, passenger car diesel oils, heavy duty diesel oils, air compressor lubricants, gear oils, aircraft turbine oils and the like, wherein the incorporation of an antioxidant in the associated lubricant additive package for the purpose of maintaining oxidative and thermal stability of the crankcase lubricating oil formulation to at least 20 minutes as measured by BPDSC at 220° C. and under 3.445 MPa (500 psi) air can be either substantially reduced or eliminated versus the amount of antioxidants used in lubricants formed from other simple esters based on other branched and/or linear alcohols and, in many cases, exhibit similar or greater stability than polyol esters, to obtain a similar HPDSC level. Furthermore, ester base stocks formed from the esterification process according to the present invention also uniquely exhibit lower metals content, lower ash content, lower total acid number and higher electrical resistivity, than other simple esters formed using a different esterification process than that recited in the present invention. The synthetic ester composition can also be a complex alcohol ester or a blend of esters, so long as the complex alcohol ester or blend of esters include 3,5,5-trimethyl-1-hexanol.

BACKGROUND OF THE INVENTION

Lubricants in commercial use today are prepared from a variety of natural and synthetic base stocks admixed with various additive packages and solvents depending upon their intended application. The base stocks typically include mineral oils, highly refined mineral oils, poly alpha olefins (PAO), polyalkylene glycols (PAG), phosphate esters, silicone esters, diesters and polyol esters.

Stability requirements and the need for lubricating oils with greater stability have been increasing. As engines become smaller and tighter, and engine operating temperatures go higher, the need for higher stability lubricants has increased. In addition, higher stability lubricants are also desired when longer drain intervals and decreased maintenance are desired, both of which result in savings.

In end uses where higher stability is desired or required, polyol esters have been commonly used due to their high thermal and oxidative stability. One of the most demanding lubricant applications in terms of thermal and oxidative requirements is oils for aircraft turbines. In aircraft turbines, where operating temperatures and exposure to oxygen are both high, it has been the industry's practice to use polyol esters. However, the high cost of polyol esters has limited their penetration thus far into other less premium markets. Polyol esters are, however, being increasingly employed as components in fully synthetic passenger car motor oils.

Most lubricating oil formulations, such as passenger car motor oils, require the addition of antioxidants (also known as oxidation inhibitors). Antioxidants retard the rate at which ester base stocks (or any base stocks) deteriorate in service, which deterioration can be evidenced by the products of oxidation such as sludge and varnish-like deposits on the metal surfaces, and by viscosity and acidity growth. Such antioxidants include arylamines (e.g., dioctyl phenylamine and phenylalphanaphthylamine), phosphosulfurized or sulfurized hydrocarbons, and hindered phenols (e.g., butylated hydroxy toluene) and the like.

Frequently replacing the lubricating oil or adding an antioxidant to suppress oxidation increases the total cost of maintaining an engine or other mechanical device. It would be most desirable to have an ester base stock which is less costly than polyol esters and exhibits substantially enhanced thermal/oxidative stability compared to conventional ester base stocks, thus requiring less frequent replacement due to decomposition (i.e., oxidation degradation). It would also be economically desirable to eliminate or reduce the amount of antioxidant which is normally added to conventional ester base stocks.

Finally, it would be desirable to have an ester base stock which exhibits low metals, low ash, lower total acid number, and high volume resistivity in order to enhance the lubricity and to reduce the corrosive effect thereof.

High Pressure Differential Scanning Calorimetry (HPDSC) has been used to evaluate the thermal/oxidative stabilities of formulated automotive lubricating oils (see J. A. Walker, W. Tsang, SAE 801383), of synthetic lubricating oils (see M. Wakakura, T. Sato, Journal of Japanese Petroleum Institute, 24 (6), pp. 383–392 (1981)) and of polyol ester derived lubricating oils (see A. Zeeman, Thermochim. Acta, 80(1984)1). In these evaluations, the time for the bulk oil to oxidize, which is the induction time, was measured. Longer induction times have been shown to correspond to more stable oils, to oils having higher concentrations of antioxidants, to oils having more effective antioxidants, or to oils having more stable base stocks. For automotive lubricants, higher induction times have been correlated with viscosity break point times.

The use of HPDSC as described herein provides a measure of stability through oxidative induction times. An ester can be blended with a constant amount of dioctyl diphenylamine which is an antioxidant. This fixed amount of antioxidant provides a constant level of protection for any ester base stock against bulk oxidation. Thus, oils tested in this manner with longer induction times have greater intrinsic resistance to oxidation.

The present inventors have developed a unique ester composition and method for preparing these esters such that they have enhanced thermal/oxidative stability, higher electrical resistivity, low metals, low ash and low total acid number, when compared to conventional ester compositions. This was accomplished by synthesizing an ester composition from 3,5,5-trimethyl-1-hexanol and either an acid or anhydride followed by the addition of an adsorbent to the ester reaction product causing the resultant ester product to have low metals, low ash, low total acid and high electrical resistivity. Complex alcohol esters can also be formed from 3,5,5-trimethyl-1-hexanol, a polyol and either a diacid or anhydride of a diacid. As the examples set forth hereafter demonstrate, the use of 3,5,5-trimethyl-1-hexanol as the alcohol in the formation of esters provide enhanced thermal and oxidative properties to otherwise low stability esters.

The thermal and oxidative stability which is designed into the novel ester compositions of the present invention eliminates or reduces the level of antioxidant which must be added to a particular lubricant, thereby providing a substantial cost savings to lubricant manufacturers.

U.S. Pat. No. 5,211,884 (Bunemann et al.), which issued on May 18, 1993, discloses a lubricant/working fluid composition (i.e., a refrigeration working fluid) for use in mechanical vapor compression type heat transfer devices.

The refrigeration working fluid is preferably tetrafluoroethane and the lubricant is an ester which is miscible with the working fluid at 10% over a temperature range of −50° C. to +80° C. and has a viscosity of 5 to 100 cSt at 40° C. Useful esters include pentaerythritol partial esters of straight chain $C_5$ or branched chain $C_7$ carboxylic acids. The lubricant may be an ester of an alkanol or of a polyol, but not both. Suitable alkanols are those containing 4 to 18 carbon atoms in a straight or branched, saturated or unsaturated hydrocarbon chain. Typical examples include iso-octanol and 3,5,5-trimethylhexanol. The alkanol or polyol may be alkoxylated, such as ethoxylated, to improve its miscibility and viscosity. The most preferred ester according to Bunemann et al. patent is a partial ester of pentaerythritol with a $C_7$ branched carboxylic acid containing approximately 90% by weight of the tetraester and 10% by weight of the triester. Other ingredients which may optionally be present in the composition include the usual additives, such as antioxidants, corrosion inhibitors, metal deactivators, lubricity additives, viscosity index improvers and extreme pressure additives as required. The only esters of Bunemann et al. which were demonstrated in the examples to exhibit satisfactory miscibility and viscosity requirements were (1) a partial pentaerythritol ester of a $C_5$ carboxylic acid, (2) a partial pentaerythritol ester of a $C_7$ carboxylic acid, (3) a pentaerythritol ester of straight chain $C_5$ and $C_8$ and branched $C_7$ and $C_8$ carboxylic acids, and (4) a trimethylolpropanol ester of straight chain $C_5$ and $C_8$ and branched $C_7$ and $C_8$ carboxylic acids.

The synthetic ester compositions according to the present invention having enhanced thermal and oxidative stability, low metals, low ash, lower acid number, and higher volume resistivity are neither described nor suggested by the partial esters of U.S. Pat. No. 5,211,884. Moreover, U.S. Pat. No. 5,211,884 pertains solely to refrigeration working fluids and is not directed to the specific lubricants recited in the present invention and to the reduction in antioxidants required thereby due to the enhanced oxidative stability of the synthetic ester compositions of the present invention. Furthermore, U.S. Pat. No. 5,211,884 does not teach how to prepare a synthetic ester having low metals, low ash, low total acid number and high electrical resistivity.

Reduction of the metals, ash, and total acid number in esters is disclosed in U.S. Pat. No. 5,185,092 (Fukuda et al.), which issued on Feb. 9, 1993, and which is incorporated herein by reference. However, Fukuda et al. is directed to a completely different application, i.e., a lubricating oil for use in refrigeration systems, and to a completely different ester, i.e., polyol esters; whereas the present invention is directed to a very specific simple and/or complex ester which utilizes 3,5,5-trimethyl-1-hexanol and exhibits a thermal and oxidative stability measured by HPDSC of greater than 20 minutes. Fukuda et al. does not teach the unique ester of the present invention which exhibits thermal and oxidative stability that can reduce or eliminate the amount of antioxidant which is required in the lubricant formulation. To the contrary, Fukuda et al. specifically states that it is preferable to use such an antioxidant in a ratio to base oil of 0.01% to 10%.

The present invention also provides many additional advantages which shall become apparent as described below.

SUMMARY OF THE INVENTION

A synthetic ester composition exhibiting thermal and oxidative stability which comprises the reaction product of 3,5,5-trimethyl-1-hexanol and at least one acid or anhydride. Optionally, the 3,5,5-trimethyl-1-hexanol can be esterified together with a polyhydroxy compound and a polycarboxylic acid or an anhydride of a polycarboxylic acid to form a complex ester. The preferred synthetic ester compositions according to the present invention have a low metals (i.e., approximately 10 ppm or less metals based on the total ester product), low ash (i.e., approximately 15 ppm or less ash based on the total ester product), low total acid number (TAN) (i.e., approximately 0.05 mg KOH/g, or less for simple esters and less than 2 for complex alcohol esters), and high volume resistivity (i.e., at least about $1\times10^{11}$, more preferably at least about $1\times10^{13}$ ohm cm).

The resultant synthetic ester composition according to the present invention exhibits a thermal/oxidative stability measured by HPDSC at 220° C., 3.445 MPa air and 0.5 wt. % Vanlube® 81 antioxidant (i.e., dioctyl diphenyl amine) of greater than 20 minutes, preferably greater than 25 minutes. The thermal/oxidative stability exhibited by the synthetic ester composition of the present invention is sufficient to either eliminate or substantially reduce the amount of antioxidant required for most lubricant formulations, thereby substantially reducing the material cost of formulating a lubricant without any antioxidant.

The present invention also includes a lubricant which is prepared from at least one synthetic ester composition exhibiting thermal and oxidative stability which comprises the reaction product of 3,5,5-trimethyl-1-hexanol and an acid or anhydride, and a lubricant additive package; whereby the incorporation of an antioxidant in the lubricant additive package for the purpose of maintaining oxidative and thermal stability of the crankcase lubricating oil formulation to at least 20 minutes as measured by HPDSC at 220° C., 3.445 MPa air and 0.5 wt. % dioctyl diphenyl amine can be either reduced or eliminated. The synthetic ester composition preferably exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1\times10^{11}$ ohm cm, more preferably at least about $1\times10^{13}$ ohm cm. Additionally, a solvent may also be added to the lubricant, wherein the lubricant comprises about 60–99% by weight of the synthetic ester composition, about 1 to 20% by weight the additive package, and about 0 to 20% by weight of the solvent.

The lubricant is preferably one selected from the group consisting of: crankcase engine oils, two-cycle engine oils, gear oils, hydraulic fluids, drilling fluids, turbine oils, greases, compressor oils, functional fluids and the like.

The additive package comprises at least one additive selected from the group consisting of: viscosity index improvers, corrosion inhibitors, antioxidants, dispersants, lube oil flow improvers, detergents and rust inhibitors, pour point depressants, anti-foaming agents, anti-wear agents, seal swellants, friction modifiers, extreme pressure agents, color stabilizers, demulsifiers, wetting agents, water loss improving agents, bactericides, drill bit lubricants, thickeners or gellants, anti-emulsifying agents, metal deactivators, and additive solubilizers. A unique feature of the ester compositions formed according to the present invention is that the amount of antioxidant additive which much be added to the lubricant consisting of such a synthetic ester composition can be substantially reduced or eliminated, as compared to the amount of antioxidant used in other lubricants formed from conventional simple esters to obtain the same oxidative stability, due to the enhanced internal oxidative stability of the esters of the present invention.

Still other lubricants can be formed according to the present invention by blending this unique synthetic ester composition and at least one additional base stock selected from the group consisting of: mineral oils, highly refined mineral oils, poly alpha olefins, polyalkylene glycols, phosphate esters, silicone oils, diesters, polyisobutylenes and polyol esters.

The present invention also involves a process for preparing a synthetic ester composition which comprises the steps of reacting 3,5,5-trimethyl-1-hexanol with at least one acid or anhydride, with or without an esterification catalyst, at a temperature in the range between about 140° to 250° C. and a pressure in the range between about 30 mm Hg to 760 mm Hg, (3.999 to 101.308 kPa) for about 0.1 to 12 hours, preferably 0.25 to 8 hours, most preferably 2 to 8 hours. This step is preferably followed by the addition of adsorbents to the ester product, thereby allowing the formation of an ester product having low metals, low ash, low total acid and high volume resistivity.

DESCRIPTION OF THE PREFERRED EMBODIMENTS

An esterification process used to make esters such as phthalates, adipates, trimellitates, isophthalates, terephthalates, acetates, propionates, carbonates, sebacates, oxo acid esters, complex acid esters, and linear acid esters comprises the reaction of 3,5,5-trimethyl-1-hexanol with at least one acid or anhydride, wherein the synthetic ester composition preferably exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1\times10^{11}$ ohm cm, more preferably at least about $1\times10^{13}$ ohm cm. Complex alcohol esters may be formed according to the present invention by the reaction of 3,5,5-trimethyl-1-hexanol, a polyhydroxy compound (i.e., a polyol) and either a polycarboxylic acid or an anhydride of a polycarboxylic acid. The composition of the feed acid is adjusted so as to provide the desired composition of the ester product.

This process includes the following steps:

(a) esterification of an acid or anhydride with excess 3,5,5-trimethyl-1-hexanol and with or without a sulfuric acid, phosphorus acid, sulfonic acid, para-toluene sulfuric acid or titanium, zirconium or tin-based catalyst at a temperature in the range between about 140° to 250° C. and a pressure in the range between about 30 mm Hg to 760 mm Hg (3.999 to 101.308 kPa) for about 0.1 to 12 hours, preferably 0.25 to 8 hours, most preferably 2 to 8 hours. The stoichiometry in the reactor is variable, with the capability of vacuum stripping excess alcohol to generate the preferred final composition;

(b) addition of adsorbents such as alumina, silica gel, zeolites, activated carbon, clay and/or filter aid to the reaction mixture following esterification before further treatment, but in certain cases clay treatment may occur later in the process following either flash drying or steam or nitrogen stripping;

(c) addition of water and base to simultaneously neutralize the residual organic and mineral acids and/or hydrolyze the catalyst and, optionally, addition of activated carbon during hydrolysis;

(d) removal of the water used in the hydrolysis step by heat and vacuum in a flash step;

(e) filtration of solids from the ester mixture containing the bulk of the excess alcohol used in the esterification reaction;

(f) removal of excess alcohol by steam stripping or any other distillation method and recycling of the alcohol to the reaction vessel; and (g) removing any residual solids from the stripped ester in a final filtration.

The addition of adsorbents such as alumina, silica gel, zeolites, activated carbon, clay and/or filter aid to the reaction mixture following esterification as described in step (b) above, allows for the formation of an ester product having low metals (i.e., approximately 10 ppm or less metals based on the total ester product), low ash (i.e., approximately 15 ppm or less ash based on the total ester product), low total acid number (TAN) (i.e., approximately 0.05 mg KOH/g or less for simple esters and less than 2 for complex esters), and high volume resistivity (i.e., at least about $1\times10^{11}$ ohm cm, more preferably at least about $1\times10^{13}$ ohm cm).

When it is desirable to use esterification catalysts, titanium, zirconium and tin-based catalysts such as titanium, zirconium and tin alcoholates, carboxylates and chelates are preferred. See U.S. Pat. Nos. 3,056,818 (Werber) and 5,324,853 (Jones et al.) which disclose various specific catalysts which may be used in the esterification process of the present invention and which are incorporated herein by reference. It is also possible to use sulfuric acid, phosphorus acid, sulfonic acid and para-toluene sulfuric acid as the esterification catalyst, although they are not as preferred as the metal catalysts discussed immediately above.

ACIDS

Carboxylic acids which undergo esterification can be aliphatic, cyclo-aliphatic or aromatic, they can be substituted or unsubstituted, saturated or unsaturated, or they can be blends of acids. Representative acids include acetic, hydroxyacetic, chloroacetic, bromoacetic, cyanoacetic, 5-phenylacetic, triphenyl acetic, propionic, halopropionic, lactic, beta-hydroxy propionic, n-butyric, isobutyric, n-valeric, isovaleric, 2-methyl valeric, 5-phenyl-n-valeric, n-heptanoic, caproic, pelargonic, caprylic, lauric, palmitic, lignoceric, alpha-hydroxy lignoceric, malonic, succinic, glutaric, adipic, pimelic, azelaic, sebacic, decane-1,10-dicarboxylic, dodecane-1, 12-dicarboxylic, pentadecane-1, 15-dicarboxylic, pentacosane-1,25-dicarboxylic, 1,2,3-propane tricarboxylic, citric, acrylic, alphachloro acrylic, beta-chloro acrylic, beta-bromo acrylic, beta-phenyl acrylic, methacrylic, vinyl acetic, crotonic, angelic, tiglic, undecylenic, oleic, erucic, linoleic, linolenic, maleic, fumaric, mesaconic, citraconic, itaconic, mucconic, aconitic, myristic, stearic, isostearic, branched $C_5$–$C_{21}$ acids. One preferred acid is a branched $C_9$ acid (i.e., 3,5,5-trimethylhexanoic acid).

Among the alicyclic acids are cyclopropane carboxylic, cyclobutane carboxylic, cyclopentane carboxylic, cycloheptane carboxylic, cyclohexane carboxylic, 2-hydroxy cyclohexane carboxylic, 1,1-cyclopropane dicarboxylic, 1,2-cyclobutane dicarboxylic, 1,3-cyclobutane dicarboxylic, 1,4-cyclohexane dicarboxylic, cyclohexane-1,2,3,4,5,6-hexacarboxylic, cyclopentene-2-carboxylic, 1-cyclohexene-1-carboxylic, hydrocapric, cyclohexadiene-1,2-dicarboxylic, and 1,3-cyclohexadiene-1,4-dicarboxylic.

The aromatic acids include benzoic, o-, m- and p-chloro and bromo benzoic, o-, m- and p-hydroxy benzoic, o-, m- and p-nitrobenzoic, o-, m- and p-methoxy benzoic, alphanaphthoic, beta-naphthoic, o-, m- and p-methyl benzoic, o-, m- and p-ethyl benzoic, p-phenyl benzoic, phthalic, isophthalic, terephthalic, hydroxy phthalic, 2,3-dimethyl benzoic, benzene-1,2,4-tricarboxylic, benzene-1,3,5-tricarboxylic, benzene-1,2,4,5-tetracarboxylic, diacids of naphthalenes and trimellitic anhydride, and trimellitic acid.

Generally, the acids are monocarboxylic acids. Suitable straight chain acids include, but are not limited to, valeric acid ($C_5$), oenanthic acid ($C_7$), caprylic acid ($C_8$), pelargonic acid ($C_9$), and capric acid ($C_{10}$). The branched chain acids may be iso-$C_5$, iso-$C_6$, iso-$C_7$, iso-$C_8$ or iso-$C_9$. Preferably, the branched acid used is the iso-$C_6$ and/or iso-$C_7$ acid. Another preferred branched acid is 3,5,5-trimethylhexanoic acid derived from the oxonation/oxidation of di-isobutylene. Still another preferred branched acid is oxo-octanoic acid derived from the oxonation/oxidation of mixed heptenes.

Selected diacids include any $C_2$ to $C_{12}$ diacids, e.g., adipic, azelaic, sebacic and dodecanedioic acids.

Carbonic acid may be used to form carbonate esters according to the present invention. However, since carbonic acid is highly unstable it is preferable to form esters of carbonic acid by reacting the alcohol, which is intended to be esterified, with, for example, carbon monoxide and oxygen in the presence of a catalyst. One such reaction procedure is disclosed in U.S. Pat. No. 4,218,391 (Romano et al.) which issued on Aug. 19, 1980, and which is incorporated herein by reference. The esterification acid can be any carbonic acid precursor or surrogate which is formed in-situ by the catalytic reaction of, for example, (a) carbon monoxide and oxygen, (b) carbon dioxide and water, (c) $COCl_2$, and (d) $CO(NH_2)_2$.

ANHYDRIDES

Anhydrides of mono and dibasic acids can be used in place of the acids, when esters are being formed. These include acetic anhydride, propionic anhydride, n-butyric anhydride, succinic anhydride, glutaric anhydride, adipic anhydride, pimellic anhydride, maleic anhydride, mesaconic anhydride, citraconic anhydride, glutaconic anhydride, itaconic anhydride, phthalic anhydride, benzoic anhydride, nadic anhydride, methyl nadic anhydride, hexahydrophthalic anhydride, trimellitic anhydride and mixed anhydrides of monobasic acids. Another anhydride is pyromellitic dianhydride.

Complex alcohol esters (e.g., pentaerythritol/adipic acid/3,5,5-trimethyl-1-hexanol) are formed by reacting 3,5,5-trimethyl-1-hexanol with one polycarboxylic acid or an anhydride of a polycarboxylic acid (e.g., diacids or anhydrides of diacids) selected from the groups of acids set forth above and any polyol. Polyols (i.e., polyhydroxy compounds) are represented by the general formula:

$R(OH)_n$ 

wherein R is an alkyl, alkenyl or aralkyl hydrocarbyl group and n is at least 2, and can be used in place of the mono alcohols when polyol esters are desired. The hydrocarbyl group may contain from about 2 to about 20 or more carbon atoms, and the hydrocarbyl may also contain substituents such as chlorine, nitrogen and/or oxygen atoms. The polyhydroxy compounds generally will contain from about 2 to about 10 hydroxy groups and more preferably from about 2 to about 6 hydroxy groups. The polyhydroxy compound may contain one or more oxyalkylene groups and, thus, the polyhydroxy compounds include compounds such as polyether polyols. The number of carbon atoms and number of hydroxy groups contained in the polyhydroxy compound used to form the carboxylic esters may vary over a wide range.

The following alcohols are particularly useful as polyols: neopentyl glycol, 2,2-dimethylol butane, trimethylol ethane, trimethylol propane, trimethylol butane, monopentaerythritol, technical grade pentaerythritol, dipentaerythritol, ethylene glycol, propylene glycol, 1,4-butanediol and polyalkylene glycols (e.g., polyethylene glycols, polypropylene glycols, polybutylene glycols, etc., and blends thereof such as a polymerized mixture of ethylene glycol and propylene glycol).

In the reaction used to form esters, the lower boiling point reagent is typically present in an excess of about 10 to 50 mole % or more for the amount of higher boiling point reagent used. The excess lower boiling point reagent is used to force the reaction to completion. The composition of the feed acid is adjusted so as to provide the desired composition of the ester product. After the reaction is complete, the excess lower boiling point reagent is removed by stripping and additional finishing. Whether the acid or alcohol is used in excess is a function of relative boiling points. That is, whichever reagent has the lowest boiling point is typically added in excess such that is may be stripped out overhead from the esterification reactor.

The ester composition according to the present invention can either be used by itself as a lubricant base stock or in admixture with other base stocks, such as mineral oils, highly refined mineral oils, poly alpha olefins (PAO), polyalkylene glycols (PAG), phosphate esters, silicone oils, diesters, polyisobutylenes and polyol esters.

The ester composition according to the present invention can be used in the formulation of various lubricants, such as, crankcase engine oils (i.e., passenger car motor oils, heavy duty diesel motor oils, and passenger car diesel oils), two-cycle engine oils, gear oils, hydraulic fluids, drilling fluids, aircraft and other turbine oils, greases, compressor oils, functional fluids and other industrial and engine lubrication applications. The preferred lubricant is prepared from at least one synthetic ester composition which comprises the reaction product of: 3,5,5-trimethyl-1-hexanol and an acid or anhydride, and a lubricant additive package; whereby the incorporation of an antioxidant in the lubricant additive package for the purpose of maintaining oxidative and thermal stability of the crankcase lubricating oil formulation to at least 20 minutes as measured by HPDSC at 220° C., 3.445 MPa air and 0.5 wt. % dioctyl diphenyl amine can be either reduced or eliminates. The lubricating oils contemplated for use with the ester compositions of the present invention include both mineral and synthetic hydrocarbon oils of lubricating viscosity and mixtures thereof with other synthetic oils. The synthetic hydrocarbon oils include long chain alkanes such as cetanes and olefin polymers such as oligomers of hexene, octene, decene, and dodecene, etc. The other synthetic oils include (1) fully esterified ester oils, such as pentaerythritol esters of monocarboxylic acids having 2 to 20 carbon atoms or trimethylol propane esters of monocarboxylic acids having 2 to 20 carbon atoms, (2) polyacetals and (3) siloxane fluids. Especially useful among the synthetic esters are those made from polycarboxylic acids and monohydric alcohols. Also preferred are the ester fluids made by fully esterifying pentaerythritol, or mixtures thereof with di- and tri-pentaerythritol, with an aliphatic monocarboxylic acid containing from 1 to 20 carbon atoms, or mixtures of such acids.

CRANKCASE LUBRICATING OILS

The ester composition or blends thereof can be used in the formulation of crankcase lubricating oils (i.e., passenger car motor oils, heavy duty diesel motor oils, and passenger car diesel oils) for spark-ignited and compression-ignited engines. The additives listed below are typically used in such amounts so as to provide their normal attendant functions. Typical amounts for individual components are also set forth below. All the values listed are stated as mass percent active ingredient.

| ADDITIVE | MASS % (Broad) | MASS % (Preferred) |
| --- | --- | --- |
| Ashless Dispersant | 0.1–20 | 1–8 |
| Metal detergents | 0.1–15 | 0.2–9 |
| Corrosion Inhibitor | 0–5 | 0–1.5 |
| Metal dihydrocarbyl dithiophosphate | 0.1–6 | 0.1–4 |
| Supplemental anti-oxidant | 0–5 | 0.01–1.5 |
| Pour Point Depressant | 0.01–5 | 0.01–1.5 |
| Anti-Foaming Agent | 0–5 | 0.001–0.15 |
| Supplemental Anti-wear Agents | 0–0.5 | 0–0.2 |
| Friction Modifier | 0–5 | 0–1.5 |
| Viscosity Modifier | 0.01–6 | 0–4 |
| Synthetic Base Stock | Balance | Balance |

The individual additives may be incorporated into a base stock in any convenient way. Thus, each of the components can be added directly to the base stock by dispersing or dissolving it in the base stock at the desired level of concentration. Such blending may occur at ambient temperature or at an elevated temperature.

Preferably, all the additives except for the viscosity modifier and the pour point depressant are blended into a concentrate or additive package described herein as the additive package, that is subsequently blended into base stock to make finished lubricant. Use of such concentrates is conventional. The concentrate will typically be formulated to contain the additive(s) in proper amounts to provide the desired concentration in the final formulation when the concentrate is combined with a predetermined amount of base lubricant.

The concentrate is preferably made in accordance with the method described in U.S. Pat. No. 4,938,880. That patent describes making a pre-mix of ashless dispersant and metal detergents that is pre-blended at a temperature of at least about 100° C. Thereafter, the pre-mix is cooled to at least 85° C. and the additional components are added.

The final crankcase lubricating oil formulation may employ from 2 to 15 mass % and preferably 5 to 10 mass %, typically about 7 to 8 mass % of the concentrate or additive package with the remainder being base stock.

The ashless dispersant comprises an oil soluble polymeric hydrocarbon backbone having functional groups that are capable of associating with particles to be dispersed. Typically, the dispersants comprise amine, alcohol, amide, or ester polar moieties attached to the polymer backbone often via a bridging group. The ashless dispersant may be, for example, selected from oil soluble salts, esters, amino-esters, amides, imides, and oxazolines of long chain hydrocarbon substituted mono and dicarboxylic acids or their anhydrides; thiocarboxylate derivatives of long chain hydrocarbons; long chain aliphatic hydrocarbons having a polyamine attached directly thereto; and Mannich condensation products formed by condensing a long chain substituted phenol with formaldehyde and polyalkylene polyamine.

The viscosity modifier (VM) functions to impart high and low temperature operability to a lubricating oil. The VM used may have that sole function, or may be multifunctional.

Multifunctional viscosity modifiers that also function as dispersants are also known. Suitable viscosity modifiers are polyisobutylene, copolymers of ethylene and propylene and higher alpha-olefins, polymethacrylates, polyalkylmethacrylates, methacrylate copolymers, copolymers of an unsaturated dicarboxylic acid and a vinyl compound, inter polymers of styrene and acrylic esters, and partially hydrogenated copolymers of styrene/isoprene, styrene/butadiene, and isoprene/butadiene, as well as the partially hydrogenated homopolymers of butadiene and isoprene and isoprene/divinylbenzene.

Metal-containing or ash-forming detergents function both as detergents to reduce or remove deposits and as acid neutralizers or rust inhibitors, thereby reducing wear and corrosion and extending engine life. Detergents generally comprise a polar head with a long hydrophobic tail, with the polar head comprising a metal salt of an acidic organic compound. The salts may contain a substantially stoichiometric amount of the metal in which case they are usually described as normal or neutral salts, and would typically have a total base number or TBN (as may be measured by ASTM D2896) of from 0 to 80. It is possible to include large amounts of a metal base by reacting an excess of a metal compound such as an oxide or hydroxide with an acidic gas such as carbon dioxide. The resulting overbased detergent comprises neutralized detergent as the outer layer of a metal base (e.g. carbonate) micelle. Such overbased detergents may have a TBN of 150 or greater, and typically of from 250 to 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450.

Dihydrocarbyl dithiophosphate metal salts are frequently used as anti-wear and antioxidant agents. The metal may be an alkali or alkaline earth metal, or aluminum, lead, tin, molybdenum, manganese, nickel or copper. The zinc salts are most commonly used in lubricating oil in amounts of 0.1 to 10, preferably 0.2 to 2 wt. %, based upon the total weight of the lubricating oil composition. They may be prepared in accordance with known techniques by first forming a dihydrocarbyl dithiophosphoric acid (DDPA), usually by reaction of one or more alcohol or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt any basic or neutral zinc compound could be used but the oxides, hydroxides and carbonates are most generally employed. Commercial additives frequently contain an excess of zinc due to use of an excess of the basic zinc compound in the neutralization reaction.

Oxidation inhibitors or antioxidants reduce the tendency of base stocks to deteriorate in service which deterioration can be evidenced by the products of oxidation such as sludge and varnish-like deposits on the metal surfaces and by viscosity growth. Such antioxidants include hindered phenols, alkaline earth metal salts of alkylphenolthioesters having preferably $C_5$ to $C_{12}$ alkyl side chains, calcium nonylphenol sulfide, ashless oil soluble phenates and sulfurized phenates, phosphosulfurized or sulfurized hydrocarbons, phosphorous esters, metal thiocarbamates, oil soluble copper compounds as described in U.S. Pat. No. 4,867,890, and molybdenum containing compounds. One of the unique features of the ester compositions of the present invention is the fact that the amount of antioxidant which must be added to the lubricant formulation can be substantially reduced or completely eliminated and still provide a lubricant which is oxidatively stable. That is, many conventional lubricant formulation include up to 5 weight % antioxidant to attain an HPDSC of 20 minutes or greater; whereas the synthetic ester base is able to attain oxidative and thermal stability of the crankcase lubricating oil formulation of at least 20 minutes as measured by BPDSC at 220° C., 3.445 MPa air and 0.5 wt. % dioctyl diphenyl amine without the need for supplemental antioxidant or at least less antioxidant than that required by other synthetic ester base stocks to exhibit equivalent stability.

Friction modifiers may be included to improve fuel economy. Oil-soluble alkoxylated mono- and diamines are well known to improve boundary layer lubrication. The amines may be used as such or in the form of an adduct or reaction product with a boron compound such as a boric oxide, boron halide, metaborate, boric acid or a mono-, di- or trialkyl borate.

Other friction modifiers are known. Among these are esters formed by reacting carboxylic acids and anhydrides with alkanols. Other conventional friction modifiers generally consist of a polar terminal group (e.g. carboxyl or hydroxyl) covalently bonded to an oleophillic hydrocarbon chain. Esters of carboxylic acids and anhydrides with alkanols are described in U.S. Pat. No. 4,702,850. Examples of other conventional friction modifiers are described by M. Belzer in the "Journal of Tribology" (1992), Vol. 114, pp. 675–682 and M. Belzer and S. Jahanmir in "Lubrication Science" (1988), Vol. 1, pp. 3–26.

Rust inhibitors selected from the group consisting of nonionic polyoxyalkylene polyols and esters thereof, polyoxyalkylene phenols, and anionic alkyl sulfonic acids may be used.

Copper and lead bearing corrosion inhibitors may be used, but are typically not required with the formulation of the present invention. Typically such compounds are the thiadiazole polysulfides containing from 5 to 50 carbon atoms, their derivatives and polymers thereof. Derivatives of 1,3,4 thiadiazoles such as those described in U.S. Pat. Nos. 2,719,125; 2,719,126; and 3,087,932; are typical. Other similar materials are described in U.S. Pat. Nos. 3,821,236; 3,904,537; 4,097,387; 4,107,059; 4,136,043; 4,188,299; and 4,193,882. Other additives are the thio and polythio sulfonamides of thiadiazoles such as those described in UK. Patent Specification No. 1,560,830. Benzotriazoles derivatives also fall within this class of additives. When these compounds are included in the lubricating composition, they are preferably present in an amount not exceeding 0.2 wt % active ingredient.

A small amount of a demulsifying component may be used. A preferred demulsifying, component is described in EP 330,522. It is obtained by reacting an alkylene oxide with an adduct obtained by reacting a bis-epoxide with a polyhydric alcohol. The demulsifier should be used at a level not exceeding 0.1 mass % active ingredient. A treat rate of 0.001 to 0.05 mass % active ingredient is convenient.

Pour point depressants, otherwise known as lube oil flow improvers, lower the minimum temperature at which the fluid will flow or can be poured. Such additives are well known. Typical of those additives which improve the low temperature fluidity of the fluid are $C_8$ to $C_{18}$ dialkyl fumarate/vinyl acetate copolymers and polyalkylmethacrylates.

Foam control can be provided by many compounds including an antifoamant of the polysiloxane type, for example, silicone oil or polydimethyl siloxane.

Some of the above-mentioned additives can provide a multiplicity of effects; thus for example, a single additive may act as a dispersant-oxidation inhibitor. This approach is well known and does not require further elaboration.

TWO-CYCLE ENGINE OILS

The ester composition or blends of esters can be used in the formulation of two-cycle engine oils together with selected lubricant additives. The preferred two-cycle engine oil is typically formulated using the ester composition formed according to the present invention together with any conventional two-cycle engine oil additive package. In addition, blends of base stocks, as described above, may be used. The additives listed below are typically used in such amounts so as to provide their normal attendant functions. The additive package may include, but is not limited to, viscosity index improvers, corrosion inhibitors, antioxidants, coupling agents, dispersants, extreme pressure agents, color stabilizers, surfactants, diluents, detergents and rust inhibitors, pour point depressants, antifoaming agents, and anti-wear agents. The thermal and oxidative stability imparted by the ester base stock of the present invention permits, in some applications, a reduction in the amount of additives, e.g., antioxidants, in the lubricant formulation.

The two-cycle engine oil according to the present invention can employ typically about 75 to 85% base stock, about 1 to 5% solvent, with the remainder comprising an additive package.

Examples of the above additives for use in lubricants are set forth in the following documents which are incorporated herein by reference: U.S. Pat. No. 4,663,063 (Davis), which issued on May 5, 1987; U.S. Pat. No. 5,330,667 (Tiffany, III et al.), which issued on Jul. 19, 1994; U.S. Pat. No. 4,740,321 (Davis et al.), which issued on Apr. 26, 1988; U.S. Pat. No. 5,321,172 (Alexander et al.), which issued on Jun. 14, 1994; and U.S. Pat. No. 5,049,291 (Miyaji et al.), which issued on Sep. 17, 1991.

HYDRAULIC FLUIDS

The ester composition or blends thereof can be used in the formulation of hydraulic fluids together with selected lubricant additives. The preferred hydraulic fluids are typically formulated using the ester composition formed according to the present invention together with any conventional hydraulic fluid additive package. The additives listed below are typically used in such amounts so as to provide their normal attendant functions. The additive package may include, but is not limited to, viscosity index improvers, corrosion inhibitors, boundary lubrication agents, demulsifiers, pour point depressants, and antifoaming agents.

The hydraulic fluid according to the present invention can employ typically about 90 to 99% base stock, with the remainder comprising an additive package.

Other additives are disclosed in U.S. Pat. No. 4,783,274 (Jokinen et al.), which issued on Nov. 8, 1988, and which is incorporated herein by reference.

DRILLING FLUIDS

The ester composition or blends thereof can be used in the formulation of drilling fluids together with selected lubricant additives. The preferred drilling fluids are typically formulated using the ester composition formed according to the present invention together with any conventional drilling fluid additive package. The additives listed below are typically used in such amounts so as to provide their normal attendant functions. The additive package may include, but is not limited to, viscosity index improvers, corrosion inhibitors, wetting agents, water loss improving agents, bactericides, and drill bit lubricants.

The drilling fluid according to the present invention can employ typically about 60 to 90% base stock and about 5 to 25% solvent, with the remainder comprising an additive package. See U.S. Pat. No. 4,382,002 (Walker et al), which issued on May 3, 1983, and which is incorporated herein by reference.

Suitable hydrocarbon solvents include: mineral oils, particularly those paraffin base oils of good oxidation stability with a boiling range of from 200°–400° C. such as Mentor 28®, sold by Exxon Chemical Americas, Houston, Tex.; diesel and gas oils; and heavy aromatic naphtha.

GEAR OILS

The ester composition or blends thereof can be used in the formulation of gear oils together with selected lubricant additives. The preferred gear oil is typically formulated using the ester composition formed according to the present invention together with any conventional gear oil additive package. The additives listed below are typically used in such amounts so as to provide their normal attendant functions. The additive package may include, but is not limited to, dispersants, antioxidants, friction modifiers, corrosion inhibitors, anti-wear agents, pour point depressants, anti-rust agents, foam inhibitors, extreme pressure agents and viscosity index improvers.

The gear oil according to the present invention can employ typically about 75 to 99% base stock and about 0 to 10% solvent, with the remainder comprising an additive package, typically in the range between about 1 to about 15 weight percent, based on the total weight of the composition.

TURBINE OILS

The ester composition or blends thereof can be used in the formulation of turbine oils together with selected lubricant additives. The preferred turbine oil is typically formulated using the ester composition formed according to the present invention together with any conventional turbine oil additive package. The additives listed below are typically used in such amounts so as to provide their normal attendant functions. The additive package may include, but is not limited to, viscosity index improvers, corrosion inhibitors, antioxidants, thickeners, dispersants, anti-emulsifying agents, color stabilizers, detergents and rust inhibitors, and pour point depressants.

The turbine oil according to the present invention can employ typically about 95 to 99.99% base stock, with the remainder comprising an additive package, typically in the range between about 0.01 to about 5.0 weight percent each, based on the total weight of the composition.

GREASES

The ester composition or blends thereof can be used in the formulation of greases together with selected lubricant additives. The main additive found in greases is the thickening agent or gellant and differences in grease formulations have often involved this additive. Besides, the thickener or gellants, other properties and characteristics of greases can be influenced by the particular lubricating base stock and the various additives that can be used.

The preferred greases are typically formulated using the ester composition formed according to the present invention together with any conventional grease additive package. The additives listed below are typically used in such amounts so as to provide their normal attendant functions. The additive package may include, but is not limited to, viscosity index improvers, antioxidants, extreme pressure agents, detergents and rust inhibitors, pour point depressants, metal deactivators, anti-wear agents, and thickeners or gellants.

The grease according to the present invention can employ typically about 80 to 95% base stock and about 5 to 20% thickening agent or gellant, with the remainder comprising an additive package.

Typical thickening agents used in grease formulations include the alkali metal soaps, clays, polymers, asbestos, carbon black, silica gels, polyureas and aluminum complexes. Soap thickened greases are the most popular with lithium and calcium soaps being most common. Simple soap greases are formed from the alkali metal salts of long chain fatty acids with lithium 12-hydroxystearate, the predominant one formed from 12-hydroxystearic acid, lithium hydroxide monohydrate and mineral oil. Complex soap greases are also in common use and comprise metal salts of a mixture of organic acids. One typical complex soap grease found in use today is a complex lithium soap grease prepared from 12-hydroxystearic acid, lithium hydroxide monohydrate, azelaic acid and mineral oil. The lithium soaps are described and exemplified in may patents including U.S. Pat. No. 3,758,407 (Harting), which issued on Sep. 11, 1973; U.S. Pat. No. 3,791,973 (Gilani), which issued on Feb. 12, 1974; and U.S. Pat. No. 3,929,651 (Murray), which issued on Dec. 30, 1975, all of which are incorporated herein by reference together with U.S. Pat. No. 4,392,967 (Alexander), which issued on Jul. 12, 1983.

A description of the additives used in greases may be found in Boner, "Modern Lubricating Greases", 1976, Chapter 5, which is incorporated herein by reference, as well as additives listed above in the other products.

COMPRESSOR OILS

The ester composition or blends thereof can be used in the formulation of compressor oils together with selected lubricant additives. The preferred compressor oil is typically formulated using the ester composition formed according to the present invention together with any conventional compressor oil additive package. The additives listed below are typically used in such amounts so as to provide their normal attendant functions. The additive package may include, but is not limited to, antioxidants, additive solubilizers, rust inhibitors/metal passivators, demulsifying agents, and anti-wear agents.

The compressor oil according to the present invention can employ typically about 80 to 99% base stock and about 1 to 15% solvent, with the remainder comprising an additive package.

The additives for compressor oils are also set forth in U.S. Pat. No. 5,156,759 (Culpon, Jr.), which issued on Oct. 20, 1992, and which is incorporated herein by reference.

It is extremely important in many lubricant applications such as aircraft turbine oils to provide a lubricant product which is thermally/oxidatively stable. One means of measuring relative thermal/oxidative stability in lubricants is via high pressure differential scanning calorimetry (HPDSC). In the tests set forth hereafter, the samples are heated to a fixed temperature and held there under a pressure of air (or oxygen) and the time to onset of decomposition is measured. The longer the time to decomposition, the more stable the sample.

EXAMPLE 1

Data from high pressure differential scanning calorimetry (HPDSC) for the esters of the present invention are given below in Table 1. For comparison purposes, data on other simple esters are also given, along with data on a number of polyol esters. All data were obtained at 220° C., in the presence of 3.445 NPa (500 PSI) instrument grade air, with 0.5 weight % of an amine antioxidant (i.e., dioctyl diphenyl amine (Vanlube® 81). Heat release/gain as a function of time is monitored, and the point where the curve begins to tread upward, called the onset of decomposition, is taken as a relative indication of the oxidative stability of the material. For a typical ester, such as diisooctyl adipate or diisooctyl phthalate, the onset of decomposition occurs around 6–15 minutes. For simple esters based on 3,5,5-trimethyl-1-hexanol, onset of decomposition times ranged between 34 minutes for the adipate up to almost 110 minutes for the phthalate, with iso-phthalate esters falling somewhere in between.

TABLE 1

| Synthetic Ester Base Stock | HPDSC (min.) |
| --- | --- |
| Adipate of 3,5,5-trimethyl-1-hexanol | 34.80 |
| Di-isooctyl adipate | 9.95 |
| Di-isononyl adipate | 6.25 |
| Phthalate of 3,5,5-trimethyl-1-hexanol | 107.71 |
| Di-isooctyl phthalate | 10.90 |
| Di-isononyl phthalate | 6.97 |
| Iso-phthalate of 3,5,5-trimethyl-1-hexanol | 34.04 |
| Neo Pentyl Glycol/3,5,5-trimethyl hexanoic acid | 99.73 |
| Trimethylolpropane/3,5,5-trimethyl hexanoic acid | 118.64 |
| Trimethylolpropane/n-C$_7$ | 34.14 |
| Trimethylolpropane/n-C$_7$/n-C$_{8/10}$ | 20.00 |
| Technical Grade Pentaerythritol/isooctanoic acid | 10.25 |
| Carbonate ester of 3,5,5-trimethyl-1-hexanol | 26.50 |
| Carbonate ester of a branched C$_9$ alcohol | 20.94* | n-C$_7$ is a normal linear acid having 7 carbon atoms.
n-C$_{8/10}$ is mixture of linear C$_8$ and C$_{10}$ acids.
Isooctanoic acid is a branched acid mixture of C$_8$ acids derived from oxonation/oxidation of mixed heptenes.
Isononyl alcohol is a branched alcohol mixture of C$_9$ alcohols derived from oxonation/oxidation of mixed octenes.
*denotes that this data was obtained at 190° C. since it would be virtually impossible to obtain an HPDSC reading at 220° C. For every 10° C. decrease in temperature, the HPDSC is typically doubled or tripled, i.e., at 220° C. this carbonate ester of a branched C$_9$ alcohol would have exhibited an HPDSC of approximately 1–3 minutes).

As the data set forth above demonstrate, simple esters based on 3,5,5-trimethyl-1-hexanol exhibit exceptional oxidative stability as measured by HPDSC. Compared to other simple esters of branched alcohols of comparable carbon number, such as di-isooctyl adipate or di-isononyl phthalate, 3,5,5-trimethyl-1-hexanol esters exhibited stabilities that are 4–5 times better. Simple esters of 3,5,5-trimethyl-1-hexanol are in terms of oxidative stability at least equal to and, in some cases, better than polyol esters.

Carbonate esters of branched C$_9$ and 3,5,5-trimethyl-1-hexanol, although they have identical carbon numbers, demonstrated substantially different onset to decomposition times as measured by HPDSC even through the carbonate esters are both formed by branched C$_9$ alcohols (i.e., 20.94 minutes at 190° C. versus 26.50 minutes at 220° C.). This clearly demonstrates the dramatic advantage of forming esters using 3,5,5-trimethyl-1-hexanol.

EXAMPLE 2

This example clearly demonstrates the difference between the thermal/oxidative stability exhibited by the synthetic ester base stock formed according to the present invention and conventional synthetic ester base stocks, and why the antioxidants can be either eliminated or substantially reduced from lubricant formulations which incorporate the synthetic ester base stock of the present invention. Table 2 below compares various trimellitic, terephthalic and phthalic esters prepared using 3,5,5-trimethyl-1-hexanol or isononyl alcohol. Each sample was evaluated for the onset time before decomposition of the ester occurs. The onset time was determined by means of high pressure differential scanning calorimetry (HPDSC). All data were obtained at 220° C. in the presence of 3.445 MPa (500 psi) air (i.e., equivalent to ca. 0.689 MPa (100 psi) oxygen) and 0.5 weight % Vanlube® 81 (i.e., a dioctyl diphenyl amine antioxidant).

TABLE 2

| Sample No. | Ester Composition | | HPDSC (min.) |
| --- | --- | --- | --- |
| | Alcohol | Acid/Anhydride | |
| 1 | 3,5,5-trimethyl-1-hexanol | trimellitic ahhydride | 88.34 |
| 2 | isononyl alcohol | trimellitic anhydride | 7.71 |
| 3 | 3,5,5-trimethyl-1-hexanol | terephthalic acid | 54.36 |
| 4 | isononyl alcohol | phthalic anhydride | 6.97 |

Again, we have demonstrated that simple esters prepared using 3,5,5-trimethyl-1-hexanol unexpectedly exhibit very good oxidative stability. This is especially true when esters formed using 3,5,5-trimethyl-1-hexanol are compared to other simple esters of C$_9$ alcohol such as those set forth in sample nos. 2 and 4.

EXAMPLE 3

Oxidation and corrosion testing was carried out on the 3,5,5-trimethyl hexyl adipate, phthalate, isophthalate and trimellitate esters. In all cases the standard for comparison was the conventional polyol ester (i.e., a mixed heptanoate, octanoate, and decanoate ester of trimethylol propane).

The oxidation and corrosion test is defined in the Military Specification No. 23699D employed to qualify base stocks for aircraft turbine oils. Six test coupons (Cu, Mg, Al, Fe, Ag and Ti) were placed in the test oil. Air flow was set at 5.0 l/hr through the oil and the temperature was held at ca. 218° C. (425° F.) for 48 hours. In addition to a visual inspection of the coupons, the coupons were weighed before and after the test and the weight change was recorded. A pass was defined as a weight change of less than −1.0 mg/cm$^2$ for Cu and Mg and less than 0.2 mg/cm$^2$ for the other metals. Finally, the weight loss of the oil (through volatilization) was measured.

The results of the corrosion test are summarized in table 3 below:

TABLE 3

| Coupon | 3,5,5-TMH Adipate | 3,5,5-TMH Phthalate | 3,5,5-TMH Trimellitate | 3,5,5-TMH Isophthalate | Mixed TMP* |
|---|---|---|---|---|---|
| Cu | Fail | Pass | Pass | Fail | Pass |
| Mg | Fail | Pass | Pass | Pass | Pass |
| Al | Fail | Pass | Pass | Pass | Pass |
| Fe | Pass | Pass | Pass | Pass | Pass |
| Ag | Fail | Pass | Pass | Pass | Pass |
| Ti | Fail | Pass | Pass | Pass | Pass |
| HPDSC** (Min.) | 35 | 107 | 88 | 34 | 23 |

*Is a mixture of heptanoate, octanoate and decanoate esters of trimethylol propane.
**HPDSC was run at 220° C., in the presence of 1.378 MPa (200 psi) oxygen and 2.067 MPa (300 psi) nitrogen, with 0.5 weight % of an amine antioxidant (i.e., dioctyl diphenyl amine (Vanlube ® 81).

The visual observation was that the trimellitate and phthalate ester samples each provided coupons which appear cleaner than the conventional mixture of heptanoate, octanoate and decanoate esters of TMP. The phthalate ester sample also exhibited some crystal formation at the top of the condenser and at the top of the reactor tube. The above data confirms the stability imparted to esters such as phthalates and trimellitates by the 3,5,5-trimethyl-1-hexanol. Both the HPDSC and the OCS (i.e., Oxidation Corrosion Stability Test) results suggest that these esters are at least comparable in stability to a trimethylol propane ester of a mix of n-heptanoic, n-octanoic and n-decanoic acids, and far more stable than other $C_7$–$C_{10}$ branched esters of the same acids.

EXAMPLE 4

A series of inclined panel deposit tests (IPDT) were run such that 80 grams of three lubricating oils (i.e., (a) a mixture of heptanoate, octanoate and decanoate esters of trimethylol propane, (b) 3,5,5-trimethyl hexyl adipate and (c) 3,5,5-trimethyl hexyl carbonate) were dripped at a rate of 2 ml/minute for ten hours onto a heated (232° C.) inclined aluminum panel. The lubricating oil from each run was recycled. At the end of the ten hours, the panel was cooled overnight and rinsed with heptane solvent. The weight of the panel was taken before and after the test. Each of the aforementioned esters exhibited less than 0.1 mg of deposit. The spent lubricating oils were then analyzed for Kinematic Viscosity at 40° C. and 100° C. The delta viscosity for the esters was as follows: mixture of heptanoate, octanoate and decanoate esters of trimethylol propane was 24%, 3,5,5-trimethyl hexyl adipate was 5% and 3,5,5-trimethyl hexyl carbonate was 1%. The delta viscosity is a measure of stability, whereby the smaller the delta, the greater the stability.

EXAMPLE 5

Complex alcohol esters of 3,5,5-trimethylhexanol were prepared by reacting a polyol, a dicarboxylic acid, and 3,5,5-trimethylhexanol, in the molar ratios given in table 4 below, in the presence of a catalyst. After reaction was complete, the catalyst was removed and excess alcohol stripped from the crude product. Filtering gives the final product.

TABLE 4

| Polyol | Dicarboxylic Acid | Alcohol | Molar Ratio | HPDSC (min.) |
|---|---|---|---|---|
| NPG | Adipic Acid | 3,5,5-trimethylhexanol | 1:2.0:2.6 | 45.6 |
| NPG | Adipic Acid | 3,5,5-trimethylhexanol | 1:2.3:3.38 | 44.3 |
| NPG | Adipic Acid | 3,5,5-trimethylhexanol | 1:1.75:2.6 | 48.9 |
| TMP | Adipic Acid | 3,5,5-trimethylhexanol | 1:3.0:3.9 | 76.9 |
| TMP | Adipic Acid | 3,5,5-trimethylhexanol | 1:3.3:3.9 | 76.9 |
| TMP | Adipic Acid | 3,5,5-trimethylhexanol | 1:2.63:3.89 | 66.7 |

NPG denote neopentyl glycol.
TMP denotes trimethylolpropane.

As the data set forth above demonstrate, complex alcohol esters based on 3,5,5-trimethylhexanol exhibit exceptional oxidative stability as measured by HPDSC. They are significantly more stable than simple esters and even most polyol esters.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

We claim:

1. A synthetic ester composition exhibiting thermal and oxidative stability which comprises the reaction product of 3,5,5-trimethyl-1-hexanol and an acid or anhydride; wherein said synthetic ester composition exhibits the following properties: a thermal/oxidative stability, measured by HPDSC at 220° C., 3.395 MPa air and 0.5 wt. % dioctyl diphenyl amine, of at least 20 minutes; a metals content of 10 ppm or less metals based on the total synthetic ester composition; an ash content of 15 ppm or less ash based on the total synthetic ester composition; a total acid number of 0.05 mg KOH/g or less; and a volume resistivity of at least about $1\times10^{11}$ ohm cm.

2. The synthetic ester composition according to claim 1 wherein said synthetic ester composition is formed by esterification of said acid or anhydride with excess 3,5,5-trimethyl-1-hexanol and with or without a sulfuric acid, phosphorus acid, sulfonic acid, para-toluene sulfuric acid or titanium, zirconium or tin-based catalyst at a temperature in the range between about 140° to 250° C. and a pressure in the range between about 30 mm Hg to 760 mm Hg.

3. The synthetic ester composition according to claim 2 further comprising the step of adding an adsorbent to said reaction mixture following esterification.

4. The synthetic ester composition according to claim 3 wherein said adsorbent is at least one material selected from the group comprising: alumina, silica gel, activated carbon, zeolites, clay and filter aid.

5. The synthetic ester composition according to claim 2 further comprising the steps of:

addition of water and base to simultaneously neutralize the residual organic and mineral acids and/or hydrolyze said catalyst;

removal of said water used in the hydrolysis step by heat and vacuum in a flash step;

filtration of solids from said ester mixture containing the bulk of the excess alcohol used in the esterification reaction;

removal of excess alcohol by steam stripping or any other distillation method and recycling of said excess alcohol to said reaction mixture; and removing any residual solids from the stripped ester in a final filtration.

6. The synthetic ester composition according to claim 1 further comprising a polyhydroxy compound and wherein said acid or anhydride is a poly acid or anhydride of a polyacid, respectively.

7. The synthetic ester composition according to claim 6 wherein said polyhydroxy compound is represented by the formula:

R(OH)$_n$ wherein R is an alkyl, alkenyl or aralkyl hydrocarbyl group and n is at least 2.

8. The synthetic ester composition according to claim 7 wherein said polyhydroxy compound is selected from the group consisting of: neopentyl glycol, 2,2-dimethylol butane, trimethylol ethane, trimethylol propane, trimethylol butane, monopentaerythritol, technical grade pentaerythritol, dipentaerythritol, ethylene glycol, propylene glycol, 1,4-butanediol and polyalkylene glycols, and blends thereof.

9. The synthetic ester composition according to claim 1 wherein said volume resistivity is at least about $1 \times 10^{13}$ ohm cm.

10. A lubricant which is prepared from:
   at least one synthetic ester composition exhibiting thermal and oxidative stability which comprises the reaction product of: 3,5,5-trimethyl-1-hexanol and an acid or anhydride; and
   a lubricant additive package; whereby the incorporation of an antioxidant in said lubricant additive package, for the purpose of maintaining oxidative and thermal stability of said lubricant to at least 20 minutes as measured by HPDSC at 220° C., 3.395 MPa air and 0.5 wt. % dioctyl diphenyl amine, can be either reduced or eliminated.

11. The lubricant according to claim 10 wherein said synthetic ester composition exhibits the following additional properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

12. The lubricant according to claim 10 wherein said synthetic ester composition is formed by esterification of said acid or anhydride with excess 3,5,5-trimethyl-1-hexanol and with or without a sulfuric acid, phosphorus acid, sulfonic acid, para-toluene sulfuric acid or titanium, zirconium or tin-based catalyst at a temperature in the range between about 140° to 250° C. and a pressure in the range between about 30 mm Hg to 760 mm Hg.

13. The lubricant according to claim 12 further comprising the step of adding an adsorbent to said reaction mixture following esterification.

14. The lubricant according to claim 13 wherein said adsorbent is at least one material selected from the group comprising: alumina, silica gel, activated carbon, zeolites, clay and filter aid.

15. The lubricant according to claim 12 further comprising the steps of:
   addition of water and base to simultaneously neutralize the residual organic and mineral acids and/or hydrolyze said catalyst;
   removal of said water used in the hydrolysis step by heat and vacuum in a flash step;
   filtration of solids from said ester mixture containing the bulk of the excess alcohol used in the esterification reaction;
   removal of excess alcohol by steam stripping or any other distillation method and recycling of said excess alcohol to said reaction mixture; and
   removing any residual solids from the stripped ester in a final filtration.

16. The lubricant according to claim 10 further comprising a polyhydroxy compound and wherein said acid or anhydride is a polyacid or an anhydride of a polyacid.

17. The lubricant according to claim 16 wherein said polyhydroxy compound is represented by the formula:

R(OH)$_n$ wherein R is an alkyl, alkenyl or aralkyl hydrocarbyl group and n is at least 2.

18. The lubricant according to claim 17 wherein said polyhydroxy compound is selected from the group consisting of: neopentyl glycol, 2,2-dimethylol butane, trimethylol ethane, trimethylol propane, trimethylol butane, monopentaerythritol, technical grade pentaerythritol, dipentaerythritol, ethylene glycol, propylene glycol, 1,4-butanediol and polyalkylene glycols, and blends thereof.

19. The lubricant according to claim 10 wherein said lubricant is a blend of said synthetic ester composition and at least one additional base stock selected from the group consisting of mineral oils, highly refined mineral oils, poly alpha olefins, polyalkylene glycols, phosphate ester, silicone oils, diesters and polyol ester.

20. The lubricant according to claim 10 wherein said additive package comprises at least one additive selected from the group consisting of: viscosity index improvers, corrosion inhibitors, antioxidants, dispersants, lube oil flow improvers, detergents and rust inhibitors, pour point depressants, anti-foaming agents, anti-wear agents, seal swellants, friction modifiers, extreme pressure agents, color stabilizers, demulsifiers, wetting agents, water loss improving agents, bactericides, drill bit lubricants, thickeners or gellants, anti-emulsifying agents, metal deactivators, coupling agents, surfactants, and additive solubilizers.

21. A crankcase lubricating oil formulation which is prepared from:
   at least one synthetic ester composition which comprises the reaction product of: 3,5,5-trimethyl-1-hexanol and an acid or anhydride; and
   a lubricant additive package; whereby the incorporation of an antioxidant in said lubricant additive package, for the purpose of maintaining oxidative and thermal stability of said crankcase lubricating oil formulation to at least 20 minutes as measured by HPDSC at 220° C., 3.395 MPa air and 0.5 wt. % dioctyl diphenyl amine, can be either reduced or eliminated, and wherein said additive package comprises at least one additive selected from the group consisting of: ashless dispersants, metal detergents, corrosion inhibitors, metal dihydrocarbyl dithiophosphates, pour point depressants, anti-foaming agents, anti-wear agents, friction modifiers, and viscosity modifiers.

22. The formulation according to claim 21 wherein said synthetic ester composition exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

23. The formulation according to claim 21 further comprising a blend of said synthetic ester composition and at least one additional base stock selected from the group consisting of: mineral oils, highly refined mineral oils, poly alpha olefins, polyalkylene glycols, phosphate ester, silicone oils, diesters and polyol ester.

24. A two-cycle engine oil formulation which is prepared from:

at least one synthetic ester composition exhibiting thermal and oxidative stability which comprises the reaction product of: 3,5,5-trimethyl-1-hexanol and an acid or anhydride; and a lubricant additive package; whereby the incorporation of an antioxidant in said lubricant additive package, for the purpose of maintaining oxidative and thermal stability of said two-cycle engine oil formulation to at least 20 minutes as measured by HPDSC at 220° C., 3.395 MPa air and 0.5 wt. % dioctyl diphenyl amine, can be either reduced or eliminated, and wherein said additive package comprises at least one additive selected from the group consisting of: viscosity index improvers, corrosion inhibitors, coupling agents, dispersants, extreme pressure agents, color stabilizers, surfactants, diluents, detergents, and rust inhibitors, pour point depressants, antifoaming agents, and antiwear agents.

25. The formulation according to claim 24 wherein said synthetic ester composition exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

26. The formulation according to claim 24 further comprising a blend of said synthetic ester composition and at least one additional base stock selected from the group consisting of: mineral oils, highly refined mineral oils, poly alpha olefins, polyalkylene glycols, phosphate ester, silicone oils, diesters and polyol ester.

27. A hydraulic fluid formulation which is prepared from:

at least one synthetic ester composition exhibiting thermal and oxidative stability which comprises the reaction product of 3,5,5-trimethyl-1-hexanol and an acid or anhydride; and a lubricant additive package; whereby the incorporation of an antioxidant in said lubricant additive package, for the purpose of maintaining oxidative and thermal stability of said hydraulic fluid formulation to at least 20 minutes as measured by HPDSC at 220° C., 3.395 MPa air and 0.5 wt. % dioctyl diphenyl amine, can be either reduced or eliminated, and wherein said additive package comprises at least one additive selected from the group consisting of: viscosity index improvers, corrosion inhibitors, extreme pressure agents, demulsifiers, pour point depressants, and antifoaming agent.

28. The formulation according to claim 27 wherein said synthetic ester composition exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

29. The formulation according to claim 27 further comprising a blend of said synthetic ester composition and at least one additional base stock selected from the group consisting of mineral oils, highly refined mineral oils, poly alpha olefins, polyalkylene glycols, phosphate ester, silicone oils, diesters and polyol ester.

30. A drilling fluid formulation which is prepared from:

at least one synthetic ester composition exhibiting thermal and oxidative stability which comprises the reaction product of: 3,5,5-trimethyl-1-hexanol and an acid or anhydride; and a lubricant additive package; whereby the incorporation of an antioxidant in said lubricant additive package, for the purpose of maintaining oxidative and thermal stability of said drilling fluid formulation to at least 20 minutes as measured by HPDSC at 220° C., 3.395 MPa air and 0.5 wt. % dioctyl diphenyl amine, can be either reduced or eliminated, and wherein said additive package comprises at least one additive selected from the group consisting of: viscosity index improvers, corrosion inhibitors, wetting agents, water loss improving agents, bactericides, and drill bit lubricants.

31. The formulation according to claim 30 wherein said synthetic ester composition exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

32. The formulation according to claim 30 further comprising a blend of said synthetic ester composition and at least one additional base stock selected from the group consisting of: mineral oils, highly refined mineral oils, poly alpha olefins, polyalkylene glycols, phosphate ester, silicone oils, diesters and polyol ester.

33. A turbine oil formulation which is prepared from:

at least one synthetic ester composition exhibiting thermal and oxidative stability which comprises the reaction product of: 3,5,5-trimethyl-1-hexanol and an acid or anhydride; and a lubricant additive package; whereby the incorporation of an antioxidant in said lubricant additive package, for the purpose of maintaining oxidative and thermal stability of said turbine oil formulation to at least 20 minutes as measured by HPDSC at 220° C., 3.395 MPa air and 0.5 wt. % dioctyl diphenyl amine, can be either reduced or eliminated, and wherein said additive package comprises at least one additive selected from the group consisting of: viscosity index improvers, corrosion inhibitors, antioxidants, dispersants, antiemulsifying agents, color stabilizers, detergents and rust inhibitors, and pour point depressants.

34. The formulation according to claim 33 wherein said synthetic ester composition exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

35. The formulation according to claim 33 further comprising a blend of said synthetic ester composition and at least one additional base stock selected from the group consisting of: mineral oils, highly refined mineral oils, poly alpha olefins, polyalkylene glycols, phosphate ester, silicone oils, diesters and polyol ester.

36. A grease formulation which is prepared from:

at least one synthetic ester composition exhibiting thermal and oxidative stability which comprises the reaction product of: 3,5,5-trimethyl-1-hexanol and an acid or anhydride; and a lubricant additive package; whereby the incorporation of an antioxidant in said lubricant additive package, for the purpose of maintaining oxidative and thermal stability of said grease formulation to at least 20 minutes as measured by HPDSC at 220° C., 3.395 MPa air and 0.5 wt. % dioctyl diphenyl amine, can be either reduced or eliminated, and wherein said additive package comprises at least one additive selected from the group consisting of: viscosity index improvers, extreme pressure agents, detergents and rust inhibitors, pour point depressants, metal deactivators, anti-wear agents, thickeners or gellants.

37. The formulation according to claim 36 wherein said synthetic ester composition exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

38. The formulation according to claim 36 further comprising a blend of said synthetic ester composition and at least one additional base stock selected from the group consisting of: mineral oils, highly refined mineral oils, poly alpha olefins, polyalkylene glycols, phosphate ester, silicone oils, diesters and polyol ester.

39. A compressor oil formulation which is prepared from:
at least one synthetic ester composition exhibiting thermal and oxidative stability which comprises the reaction product of: 3,5,5-trimethyl-1-hexanol and an acid or anhydride; and a lubricant additive package; whereby the incorporation of an antioxidant in said lubricant additive package, for the purpose of maintaining oxidative and thermal stability of said compressor oil formulation to at least 20 minutes as measured by HPDSC at 220° C., 3.395 MPa air and 0.5 wt. % dioctyl diphenyl amine, can be either reduced or eliminated, and wherein said additive package comprises at least one additive selected from the group consisting of: additive solubilizers, rust inhibitors/metal passivators, demulsifying agents, and anti-wear agents.

40. The formulation according to claim 39 wherein said synthetic ester composition exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

41. The formulation according to claim 39 further comprising a blend of said synthetic ester composition and at least one additional base stock selected from the group consisting of: mineral oils, highly refined mineral oils, poly alpha olefins, polyalkylene glycols, phosphate ester, silicone oils, diesters and polyol ester.

42. A gear oil formulation which is prepared from:
at least one synthetic ester composition exhibiting thermal and oxidative stability which comprises the reaction product of: 3,5,5-trimethyl-1-hexanol and an acid or anhydride; and a lubricant additive package; whereby the incorporation of an antioxidant in said lubricant additive package, for the purpose of maintaining oxidative and thermal stability of said gear oil formulation to at least 20 minutes as measured by HPDSC at 220° C., 3.395 MPa air and 0.5 wt. % dioctyl diphenyl amine, can be either reduced or eliminated, and wherein said additive package comprises at least one additive selected from the group consisting of: dispersants, friction modifiers, corrosion inhibitors, anti-wear agents, pour point depressants, anti-rust agents, foam inhibitors, extreme pressure agents and viscosity index improvers.

43. The formulation according to claim 42 wherein said synthetic ester composition exhibits the following properties: a metals content of 10 ppm or less metals based on the total synthetic ester composition, an ash content of 15 ppm or less ash based on the total synthetic ester composition, a total acid number of 0.05 mg KOH/g or less, and a volume resistivity of at least about $1 \times 10^{11}$ ohm cm.

44. The formulation according to claim 42 further comprising a blend of said synthetic ester composition and at least one additional base stock selected from the group consisting of: mineral oils, highly refined mineral oils, poly alpha olefins, polyalkylene glycols, phosphate ester, silicone oils, diesters and polyol ester.

* * * * *

UNITED STATES PATENT AND TRADEMARK OFFICE
CERTIFICATE OF CORRECTION

PATENT NO.  : 5,798,319

DATED       : August 25, 1998

INVENTOR(S) : Richard H. Schlosberg, David W. Turner, Martin A. Krevalis, William J. Munley, Jr, Haven S. Aldrich It is certified that error appears in the above-identified patent and that said Letters Patent is hereby corrected as shown below:

claim 1, line 32, 3.395 MPa
should read line 32 3.445 MPa claim 10, line 33, 3.395 MPa
should read line 33 3.445 MPa claim 21, line 50, 3.395 MPa
should read line 50 3.445 MPa claim 24, line 15, 3.395 MPa
should read line 15 3.445 MPa claim 27, line 45, 3.395 MPa
should read line 45 3.445 MPa claim 30, line 7, 3.395 MPa
should read line 7 3.445 MPa

UNITED STATES PATENT AND TRADEMARK OFFICE
CERTIFICATE OF CORRECTION

PATENT NO. : 5,798,319
DATED : August 25, 1998
INVENTOR(S) : Richard H. Schlosberg, David W. Turner, Martin A. Krevalis, William J. Munley, Jr., Haven S. Alrich It is certified that error appears in the above-identified patent and that said Letters Patent is hereby corrected as shown below:

claim 33, line 37, 3.395 MPa
should read line 37 3.445 MPa claim 36, line 67, 3.395 MPa
should read line 67 3.445 MPa claim 39, line 30, 3.395 MPa
should read line 30 3.445 MPa claim 42, line 19, 3.395 MPa
should read line 19 3.445 MPa Signed and Sealed this First Day of February, 2000

Attest:

Q. TODD DICKINSON

*Attesting Officer*     *Acting Commissioner of Patents and Trademarks*